US007838238B2

(12) United States Patent
Ryo et al.

(10) Patent No.: US 7,838,238 B2
(45) Date of Patent: Nov. 23, 2010

(54) METHOD FOR SCREENING ANTI-HIV DRUGS AND A DIAGNOSTIC METHOD OF AIDS

(75) Inventors: Akihide Ryo, Tokyo (JP); Naoki Yamamoto, Tokyo (JP); Ryo Morishita, Matsuyama (JP)

(73) Assignees: CellFree Sciences Co., Ltd., Kanagawa (JP); National Institute of Infectious Diseases, Tokyo (JP)

( * ) Notice: Subject to any disclaimer, the term of this patent is extended or adjusted under 35 U.S.C. 154(b) by 0 days.

(21) Appl. No.: 12/188,242

(22) Filed: Aug. 8, 2008

(65) Prior Publication Data

US 2010/0034744 A1 Feb. 11, 2010

(51) Int. Cl.

| | |
|---|---|
| ***C12Q 1/68*** | (2006.01) |
| ***C07H 21/02*** | (2006.01) |
| ***C07H 21/04*** | (2006.01) |

(52) U.S. Cl. .......................... 435/6; 536/23.1; 536/24.5

(58) Field of Classification Search ....................... None
See application file for complete search history.

(56) References Cited

U.S. PATENT DOCUMENTS

2004/0142897 A1 * 7/2004 Waisman ..................... 514/44

OTHER PUBLICATIONS

Song et al., Suppressor of cytokine signaling 1 inhibition strategy to enhance anti-HIV vaccination, 2006, Expert Rev. Vaccines, 5(4), pp. 495-503.*

Ryo et al., "Identification of host factors involved in post-translational modifications of HIV-1 proteins using cell free protein production system," Awaji International Forum on Infection and Immunity, Sep. 1-5, 2007 (1 page).

Yamamoto, (no title), Awaji International Forum on Infection and Immunity, Sep. 4-7, 2006 (1 page).

Ryo et al., "Identification and characterization of a novel host factor for HIV-1 infection by serial analysis of gene expression (SAGE) technique," The 7$^{th}$ Kumamoto AIDS Seminar: Abstract Submission Form, Sep. 21-22, 2006 (1 page).

Ryo et al., "SOCS1 is an inducible host factor during HIV-1 infection and regulates the intracellular trafficking and stability of HIV-1 Gag," PNAS, vol. 105, No. 1, Jan. 8, 2008 (pp. 294-299).

* cited by examiner

*Primary Examiner*—Amy Bowman
(74) *Attorney, Agent, or Firm*—Kilyk & Bowersox, P.L.L.C.

(57) ABSTRACT

The present invention elucidated the interaction between host-side factors and HIV particles, and provided a method for screening anti-HIV-1 drug targeting a new host-side factor. Furthermore, the present invention provided a new diagnostic method of AIDS based on the interaction.

9 Claims, 15 Drawing Sheets

METHOD FOR SCREENING ANTI-HIV DRUGS AND A DIAGNOSTIC METHOD OF AIDS

BACKGROUND OF THE INVENTION

1. Field of the Invention

The present invention relates to a novel method for screening an anti-HIV drug, and more specifically relates to an in vivo method for screening an inhibitor against the interaction between SOCS1 and HIV-1 Gag. Furthermore, the present invention relates to a new diagnostic method of AIDS.

2. Related Background of the Invention

There are evidences that 1% of the whole world population has already infected with Human immunodeficiency virus (HIV), and the infection is still spreading steadily. At present, the number of persons infected with the pathogenic virus, HIV, has exceeded 40,000,000 all over the world, and about 5,000,000 persons are being newly infected every year. Probably because the number of persons infected with HIV and AIDS patients in Japan is less than that in European and American countries, no sufficient educational effect is attained and increase of the infected patients is exceptionally still not halted among the developed nations in the world. Though life prognoses of the patients have been improved by the establishment of a recent HAART, the number of patients under long-term medical treatment has increased, and problems of resistance to conventional drugs and new complications such as Immune Reconstitution Syndrome have appeared. In addition, complications with the other chronic infectious diseases including HCV are becoming big social problems together with the issue of HIV-tainted blood products in Japan. It is therefore becoming increasingly important and urgent to respond to the social demand for the elucidation of the mechanisms of persistent viral infection and pathogeny and take effective measures.

The interaction between host protein and HIV protein is essential for the formation of HIV infection, and the interaction itself plays an important role in the growth, life cycle and pathogenic expression mechanism of the virus. In addition, it is necessary to thoroughly understand qualitative, temporal and spatial relationships for the formation of virus-host protein interaction as one of intracellular immune response mechanism of a host individual against virus accompanied by the infection. However, in studies up to now efforts have been focused on the analysis of viral gene structure and the existing anti-AIDS drugs are mainly those targeting HIV protein. A big problem for the current treatment of HIV/AIDS patients is the appearance of drug-resistant viruses, but this problem remains unsolved as long as the easily variable HIV proteins are targeted. To overcome these problems, it is expected to develop drugs that inhibit host factors crucial for HIV replication.

The screening method targeting the above-mentioned host-side factors includes a screening system which inhibits binding of one of HIV-1 genome-encoded accessory proteins Nef with Hck (a host-side factor) (Non-patent document No. 1).

Furthermore, a method for screening an anti-HIV-1 drug comprising culturing "macrophage lineage cells expressing M-CSF receptor, and Nef-ER fusion protein prepared by the fusion of hormone-binding domain of HIV-1 Nef protein and an estrogen receptor which multiply depending on M-CSF" in the presence of an estrogen derivative, M-CSF and a candidate agent to increase the macrophage lineage cell and comparing cell growth of the macrophage lineage cell with that of macrophage lineage cell in the absent of candidate agent is known(Patent document No. 1).

In addition, as an HIV therapy, it has become possible to delay the onset of the disease through the HAART which combines reverse transcriptase inhibitors such as azidothymidine (AZT) with 2-4 protease inhibitors. However, by the appearance of a resistant virus and through adverse reactions, these drugs often have their limits in therapeutic effects.

Therefore, under the circumstances there is an urgent need to develop an anti-AIDS drug with a new action mechanism, targeting the host-side factors.

(Patent documents Nos. 2 and 3)

[Non-patent document No. 1] Murakami Y, Fukazawa H, Kobatake T, et al. A mammalian two-hybrid screening system for inhibitors of interaction between HIV Nef and the cellular tyrosine kinase Hck. Antiviral Res. 2002; 55:161-168.

[Patent document No. 1] Japanese publication of unexamined patent application No. 2006-129726

[Patent documents No. 2] Japanese publication of unexamined patent application No.2006-262749

[Patent documents No. 3] Japanese publication of unexamined patent application No.2007-312617

SUMMARY OF THE INVENTION

The present inventors assumed the problems mentioned above as the tasks to be solved. More in detail, the present invention aimed to elucidate the interaction between host-side factors and HIV particles, and to provide a method for screening anti-HIV-1 drugs targeting the new host-side factors.

In addition, the present invention aimed to provide a new diagnostic method of AIDS based on the mechanism.

The inventors of the present invention have identified a host gene and a gene product specifically induced by HIV infection through the use of Serial Analysis of Gene Expression (SAGE) method to investigate intracellular immune response of HIV-infected host cells and its related factors. As a result, it has been found that a suppressor of cytokine signaling SOCS1 is induced to specifically express in HIV-infected T cells. In addition, the inventors have confirmed that SOCS1 in the peripheral blood of persons infected with HIV without long-term onset of AIDS is significantly lower in comparison with that of patients who had AIDS and have elucidated that induction of SOCS1 gene and functions of the gene product are important for the onset of AIDS. The inventors of the present invention have also found that SOCS1 can directly interact with HIV core protein Gag.

Then, the inventors of the present invention have accomplished an in vivo method for screening an inhibitor against the interaction between SOCS1 and Gag based on these findings. Furthermore, they also have accomplished a new diagnostic method of AIDS.

That is, the present invention is as follows:

1. The methods for in vivo screening of an inhibitor against the interaction between SOCS1 and Gag comprising processes of:

1) expressing Gag or a modified Gag, and SOCS1 or a modified SOCS1 in cells;

2) introducing a candidate inhibitor into the cells; and 3) detecting changes in the interaction between SOCS1 and Gag.

2. The screening method according to the preceding item 1 comprising the processes of introducing a gene encoding the Gag or modified Gag, and/or the SOCS1 or modified SOCS1 into the cells and expressing the Gag or modified Gag, and/or the SOCS1 or modified SOCS1 in the cells.

3. The screening method according to item 1 or 2 comprising the method for detecting changes in the interaction between the SOCS1 and Gag by any one of the methods of:
   1) RT-PCR;
   2) immunoblotting;
   3) serial analysis of gene expression (SAGE);
   4) immunoprecipitation;
   5) pull-down assay;
   6) ELISA; and
   7) Western blotting.
4. The screening method according to any one of the items 1-3, wherein the inhibitor against interaction between the SOCS1 and Gag is an AIDS therapeutic agent and/or AIDS onset inhibitor.
5. A method for screening siRNA suppressing or inhibiting the interaction between SOCS1 and Gag comprising the processes of:

1) introducing SOCS1 gene or the modified SOCS1 gene into cells;

2) introducing a candidate siRNA into the cells; and 3) detecting the SOCS1 or SOCS1 gene dosage.

6. A screening method according to item 5 comprising further introducing Gag gene or the modified Gag gene into the cells.
7. A siRNA suppressing or inhibiting the interaction between SOCS1 and Gag.
8. The siRNA according to item 7 having a sequence comprising essentially any one of the followings:
   (1) Sequence No. 2;
   (2) Sequence No. 3;
   (3) Sequence No. 4;
   (4) Sequence No. 3; and
   (5) Sequence No. 6.
9. An AIDS therapeutic agent and/or an AIDS onset inhibitor containing any one or more of siRNAs according to the preceding item 8 as active ingredients.
10. A diagnostic method of AIDS comprising the processes of:

1) collecting the peripheral blood of persons infected with HIV;

2) determining the above-mentioned SOCS1 or SOCS1 gene dosage in the peripheral blood; and 3) comparing the SOCS1 or SOCS1 gene dosage with a predetermined reference value.

11. The diagnostic method according to item 10 comprising the process of predicting the onset time of persons infected with HIV.
12. The diagnostic method according to item 10 comprising the process of evaluating the degree of progression of AIDS in persons infected with HIV.

The present invention provides a new method for screening anti-HIV-1 drugs based on the interaction between SOCS1 and HIV-1 p55 Gag which has not been known. Furthermore, the present invention provides a new diagnostic method of AIDS based on the interaction.

DESCRIPTION OF THE PREFERRED EMBODIMENTS

The screening method of the present invention makes use of findings from the following Examples 1-6 that SOCS1 in HIV-infected cells is expressed more significantly than that in non-HIV-infected cells. More specifically, the method makes use of findings that SOCS1 plays a role in intracellular trafficking of HIV-1 Gag to plasma membrane, and moreover the transfer of HIV-1 Gag in cell membrane is inhibited by the inhibition of expression of SOCS1, thus resulting in breaking down HIV-1 particle in lysosomes.

Therefore, using the screening system of the present invention, an AIDS therapeutic agent and/or onset inhibitor having a new mechanism of action can be developed by the identification of a candidate drug inhibiting the interaction between SOCS1 and Gag.

The diagnostic method of AIDS of the present invention makes use of a finding that patients without any symptoms of AIDS for a long term (Long-term non-progressor: LTNP) have significantly lower levels of SOCS1 than asymptomatic carrier patients (Asymptomatic carrier: AC) and AIDS patients as shown in the following Example 7.

Therefore, according to the diagnostic method of the present invention, the prediction of the time of the disease onset and the degree of progression can be evaluated by determining the expression level of SOCS1 in the peripheral mononuclear cells of HIV infected persons.

(SOCS1)

SOCS (suppressor of cytokine signaling)-1 is an intracellular cytokine-inductive molecule. In addition, SOCS-1 is known to function as a negative feed-back factor relating to the signaling of cytokines such as IFN-γ, IL-4 and IL-2 by interacting with phosphorylated Janus kinase (JAK). In addition, SOCS has SOCS-box and SH2 domain, and more than 10 kinds of SOCSs such as SOCS1, SOCS2 and SOCS3 are known.

In addition, the screening method of the present invention targets only SOCS1 in the SOCS family. Since SOCS3, another member in the SOCS family does not enhance replication of HIV-1 as is clear from the results of Example 2, it is not included in the subject of the present invention. Furthermore, the modified SOCS1 is also included in the subject of the present invention.

The "modified SOCS1" of the present invention refers to a substance having structures where at least SOCS-box and SH2 domain structures are retained and one to several ten amino acids in the amino acid sequence are substituted, deleted, added or inserted in comparison with the structure of SOCS1. In addition, polypeptides having only SOCS-box and SH2 domain structures are also included in the modified SOCS1.

The inventors of the present invention have found that from the Example 4 described below, the interaction between SOCS1 and Gag essentially requires at least SH2 domain. That is, the screening method of the present invention does not necessarily require a full-length sequence of SOCS1.

(HIV-1 p55 Gag)

HIV-1 p55 Gag is made up of four domains essential for the growth of AIDS virus. The matured Gag protein includes matrix protein (MA/p17), capsid protein (CA/p24), nucleocapsid protein (NC/p7) and p6 domain, and further SP1 and SP2 spacer peptides. In addition, the screening method of the present invention also covers modified Gag.

The "modified Gag" of the present invention refers to a substance having structures where at least MA and NC domain structures are retained and one to several ten amino acids in the amino acid sequence are substituted, deleted added or inserted in comparison with the structure of Gag.

The inventors of the present invention found that from the Example 4 below, Gag essentially requires at least MA and NC domain for the interaction with SOCS1. That is, the screening methods of the present invention do not necessarily require a full-length sequence of Gag.

Method of introducing variations such as substitution, deletion, addition or insertion of one to several tens amino acids into the amino acid sequence is itself publicly known in general, and for example, the technology of Ulmer [Science, 219, 666-671 (1983)] can be used. For example, mutual substitutions between homologous amino acids (a polar amino acid, a non-polar amino acid, a hydrophobic amino acid, a hydrophilic amino acid, a positively-charged amino acid, a negatively-charged amino acid and an aromatic amino acid) is easily assumed in view of the fact that fundamental properties of pertinent proteins (such as physical properties, functions or immunological activity) are not altered. Furthermore, these applicable proteins can be modified to the extent that remarkable functional changes do not occur including, for example, amidating modification of structural amino group, carboxyl group or the like.

(Interaction Between SOCS1 and Gag)

The "interaction between SOCS1 and Gag" of the present invention means direct binding of SOCS1 with Gag, followed by a transfer process of the Gag to the cytoplasmic membrane. In addition, "an inhibitor against the interaction between SOCS1 and Gag" of the present invention means a substance inhibiting any of steps of the above-mentioned process, and also includes a substance inhibiting the preceding step of binding SOCS1 with Gag.

(Cells Used in the Screening System)

The cells used in the screening system of the present invention are preferably, but not specifically limited to, human-derived cells as long as they can achieve intracellular interaction between SOCS1 and Gag.

Examples of human-derived cells include human lymphocytes cell line, HeLa cells, 293T cells, or Jurkat cells.

(Method for the Expression of Gag)

Methods for expressing Gag in the above-mentioned cells include, but not specifically limited to, one introducing a HIV-1 molecular clone pNL4-3 into cells. For example, it is only necessary to introduce Gag or a modified Gag, or a gene encoding Gag or a modified Gag into the cells.

In addition, Gag can also be expressed by infecting cells used in the screening system with HIV-1.

(Method for the Expression of SOCS1)

Endogenous SOCS1 expressed in cells can be used as SOCS1. However, SOCS1 or a modified SOCS1, or a gene encoding SOCS1 or a modified SOCS1 may be introduced into the cells to build a more sensitive screening system.

Expression systems for expressing the above-mentioned Gag, a modified Gag, SOCS1, and a modified SOCS1 are publicly known to those skilled in the art. In other words, gene products encoding Gag, a modified Gag, SOCS1, and a modified SOCS1 can be introduced into publicly known protein synthesizing systems for the expression. A cell-free protein-synthesizing system, particularly cell-free wheat germ protein-synthesizing system can be used in the protein synthesis. For example, a protein synthesis kit manufactured and sold by CellFree Sciences Co., Ltd. (http://www.cfsciences.com/eq/business.html) can be included.

Then, Gag, a modified Gag, SOCS1 and a modified SOCS1 expressed in the protein-synthesizing system may be introduced into the screening cells.

In addition, the genes of above mentioned Gag, a modified Gag, SOCS1 and a modified SOCS1 may be inserted in the downstream of the promoter of vector prepared by a method such as a genetic recombination method or a PCR method, and then the gene recombinant expression vector may be introduced into the screening cells.

The methods for introducing the above-mentioned recombinant expression vector into a host include, but not limited to, for example, a calcium phosphate method, a protoplast method, an electroporation method, a spheroplast method, a lithium acetate method and a lipofection method. In addition, a retrovirus vector, a wrench virus vector and the like can preferably be used.

(Methods for the Detection of Changes in the Interaction Between SOCS1 and Gag)

As shown above, the cell system (in vivo) expressing SOCS1 or a modified SOCS1, and Gag or a modified Gag can be used as a screening system of anti-HIV-1 drugs. Specifically, inhibitors can be selected by comparing the expression level of SOCS1 and/or the level of replication of HIV-1 particles after culturing the above-mentioned screening cells in the presence or absence of candidate inhibitors.

(Determination of Expression Level of SOCS1)

The following methods themselves publicly known are exemplified as methods for determining expression level of SOCS1, but not specifically limited to them:

1) determining the SOCS1 gene dosage in cells by a RT-PCR method;

2) determining SOCS1 in cells by immunoblotting;

3) determining SOCS1 in cells by SAGE;

4) determining SOCS1 in cells by immunoprecipitation using anti-SOCS1 antibody;

5) determining SOCS1 in cells by pull-down assay;

6) determining SOCS1 in cells by ELISA; and 7) determining SOCS1 in cells by Western blotting.

(Determination of the Replicated Quantity of HIV-1 Particles)

The method for determining the quantity of replication of HIV-l particles is exemplified by, but not particularly limited to, the detection of p24 antigen in the cells using anti-p24 antibody. In addition, methods for detecting p24 antigen using p24 antibody include ELISA, immunoblotting and the like.

(Methods for the Confirmation of the Intracellular Transfer of Gag)

Methods for confirming the intracellular transfer of Gag include pulse-chase method, fluorescent immunostaining method and the like.

(Screening Methods of siRNA Inhibiting the Interaction Between SOCS1 and Gag)

A method for screening siRNA inhibiting the interaction between SOCS1 and Gag is also a subject of the present invention.

In addition, when the preceding step of the interaction between SOCS1 and Gag is targeted, the simpler screening system comprises the processes of:

1) introducing SOCS1 gene or a modified SOCS1 gene into cells;

2) introducing a candidate siRNA into the cells; and 3) detecting the SOCS1 or SOCS1 gene dosage.

Furthermore, a process of introducing Gag gene or a modified Gag gene into cells is included when the stage of combination of SOCS1 and Gag or the stage after the combination is targeted at.

(siRNA Inhibiting the Interaction Between SOCS1 and Gag)

The inventors of the present invention have already succeeded in suppressing the production of HIV-1 particles by the below-mentioned five kinds of siRNAs according to the below-mentioned Example 6.

| | | |
|---|---|---|
| siRNA I: | UCGAGCUGCUGGAGCACUA | (sequence No. 2) |
| siRAN II: | GGCCAGAACCUUCCUCUU | (sequence No. 3) |
| siRNA III: | AACCAGGUGGCAGCCGACA | (sequence No. 4) |
| siRNA IV: | ACGAGCAUCCGCGUGCACUU | (sequence No. 5) |
| siRNA V: | CUACCUGAGCUCCUUCCCC | (sequence No. 6) |

The siRNA having a sequence comprising essentially any one of the above siRNAs (sequences No. 2 to 6) is also in the subject of the present invention.

The present invention also aims at an AIDS therapeutic agent and/or an AIDS onset inhibitor containing any one or more siRNAs mentioned above as active ingredients.

(Diagnostic Method of AIDS)

The diagnostic method of AIDS of the present invention as being different from the conventional one makes use of the expression level of SOCS1 in cells as an indicator. The inventors of the present invention have confirmed that the level of SOCS1 in the peripheral blood of long-term AIDS non-progressors was significantly lower than that of AIDS developed patients according to the below-mentioned Example 7 and have clarified that SOCS1 gene induction and the function of the gene product are important for the onset of AIDS. More specifically, patients with lower levels of SOCS1 in the cells are considered to exhibit a slower onset of AIDS in comparison with patients with higher levels of SOCS1 in the cells.

That is, according to "the diagnostic method of AIDS" of the present invention, the time of the disease onset can be predicted and the degree of progression can be evaluated by comparing the level of SOCS1 with a predetermined standard value.

In addition, the standard value means a reference value exhibiting the degree of progression. Generally, the level of SOCS1 in the infected cells is considered to increase with the progression of AIDS. The standard value is calculated and set by using the average levels of SOCS1 obtained from the peripheral blood of the patients whose degree of progression of AIDS and onset time is confirmed in advance.

(Candidate Inhibitors)

As candidate inhibitors for the present invention, voluntary substances can be used. The types of the candidate inhibitors are not specifically limited, but individual low-molecular-weight synthetic compounds, particularly siRNAs, compounds present in natural extracts, or synthetic peptides may be used. Furthermore, the candidate inhibitors may also be from a compound library, a phage display library or a combinatorial library. The candidate inhibitors are preferably low-molecular-weight compounds, and a compound library of low-molecular-weight compounds is preferable. Construction of the compound library is well known to those skilled in the art, and a commercial compound library may also be used.

(An AIDS Therapeutic Agent and/or an AIDS Onset Inhibitor)

The AIDS therapeutic agent and/or the AIDS onset inhibitor of the present invention contain an inhibitor against the interaction between SOCS1 and Gag as an active ingredient. More specifically, the agents (inhibitors) contain one or more siRNAs shown by the above-mentioned sequence Nos. 2-6.

Furthermore, depending on the preventive and therapeutic purposes, the agents may be prepared in various forms such as powder preparations, granules, tablets, capsules, enteric soluble preparations, liquid preparations, injection preparations (liquid and suspension preparations) or forms used in gene therapy by the conventional methods. The therapeutic agents and/or onset inhibitors of the present invention are preferably prepared as pharmaceutical compositions using one or more medicinal carriers in general.

The dosage or intake of the therapeutic agents and/or onset inhibitors of the present invention is suitably selected according to the efficacy of the contained components, the form of administration, the route of administration, the type of disease, properties of the subject (body weight, age, symptom and the presence or absence of the use of other drugs) and judgments by a doctor in charge of the patient, but is not specifically limited if the effects of the present invention can be obtained. The pharmaceutical agent or foodstuff of the present invention may be administered or ingested once every several hours, daily or every several days or weeks.

The present invention will further be practically explained using the following examples, but the scope of the present invention is not limited by these examples.

EXAMPLE 1

(Identification of Host-Side Factors Interacting with HIV-1)

SAGE (serial analysis of gene expression) was carried out using HIV-1 and MOLT-4 (human lymphocytes cell line) to elucidate the genes involved in the replication process of HIV-1 and the cellular pathway. The details are as follows.

(A) MOLT-4 cells were caused to infect with mock or HIV-$1_{NL4\text{-}3}$, and total RNA and a protein extracts derived from these cells were subjected to a semiquantitative RT-PCR and immunoblotting.

(B) PBMC (the peripheral-blood mononuclear cells) derived from two healthy individuals were caused to infect with mock or HIV-$1_{NL4\text{-}3}$. The expression level of SOCS1 in these cells was determined by a semiquantitative RT-PCR.

A predominant expression of SOCS1 gene after being infected with HIV-1 was found by a semiquantitative RT-PCR and immunoblotting using an anti-SOCS1 antibody from the results of the above-mentioned (A) (reference: FIG. 1A).

A specific and significant expression of SOCS1 in PBMC (peripheral-blood mononuclear cells) infected with HIV-1 was confirmed from the results of the above-mentioned (B) (reference: FIG. 1B).

Based on the above-mentioned results, involvement of SOCS1 in the HIV-1 replication process was found.

EXAMPLE 2

(Elucidation of the Interaction Between HIV-1 and SOCS1)

Based on the results of the above-mentioned Example 1, the interaction between SOCS1 and HIV-1 was studied. The details are as follows.

(A) 293T cells were transfected with pNL4-3 as an HIV-1 molecular clone and cotransfected with various amounts (0-1.0 μg) of pcDNA-myc-SOCS1. 48 hours after the transfection, the quantity of p24 antigen released into the supernatant of the cells was determined by ELISA using the anti-p24 antibody.

(B) 293T cells were transfected with pNL4-3 and cotransfected with control vector, SOCS1 (a wild type), SOCS1ΔS (SOCS box deleted mutant), SOCS1R105E (SH2 domain deleted mutant) or SOCS3. 48 hours after the transfection, the quantity of p24 antigen released into the supernatant of the cells was determined by ELISA using the anti-p24 antibody.

(C) The cell lysates and pelleted viruses prepared in the above-mentioned (A) were analyzed by immunoblotting.

(D) The cell lysates and pelleted viruses prepared in the above-mentioned (B) were then collected after 48 hours and subjected to immunoblotting.

The results of the above-mentioned (A) showed wild-type SOCS1 significantly increases the production of HIV-1 in the cell supernatant in a dose-dependent manner (reference: FIG. 2A upper). On the other hand, the results of the above-mentioned (B) showed no increase virus production in SOCS1R105E (SH2 domain deleted mutant) and SOCS1ΔS (SOCS box deleted mutant) in comparison with that in wild type SOCS1 (reference: FIG. 2B upper). Furthermore, SOCS3 was unable to raise the expression level of HIV-1 Gag.

The results of the above-mentioned (C) and (D) showed that neither SOCS1ΔS nor SOCS1R105E could promote virus production to the same levels as wild type.

However, in cells transfected with SOCS1ΔS and SOCS1R105E the expression level of HIV-1 increased depending on the intracellular Gag protein level. The increase was consistent with the increased level of the HIV-1 particle production in the supernatant.

The above results showed that SOCS1 has a function of increasing the production of HIV-1 particles in infected cells and moreover both SH2 domain of SOCS1 and SOCS-box domain are needed for the function.

EXAMPLE 3

(Elucidation of the Interaction Time of HIV-1 and SOCS1)

The inventors of the present invention have further observed morphologic profile of the HIV-1 particle production. Furthermore, a gene reporter assay was performed to elucidate the enhanced HIV-1 production process in the existence of SOCS1. The details are as follows:

(A) 293T cells cotransfected with pNL4-3+control vector or pNL4-3+myc-tagged SOCS1 and were fixed in glutaraldehyde. Then, the fixed 293T cells were observed using Transmission Electron Microscope (TEM).

(B) Virions obtained from control vector (EV)-introduced 293T cells or SOCS1-introduced 293T cells were introduced into Jurkat cells.

(C) The gene reporter assay was carried out under the condition of wild type HIV-LTR (pLTR-luc) or a full-length provirus vector (pNL4-3–luc).

The result of the above-mentioned (A) showed that a significantly increased number of mature virus particles were observed in SOCS1-expressing cells in comparison with the control vector-introduced cells (reference: FIG. 3A). In addition, no deformation of viral particles could be observed in SOCS1-expressed cells (reference: FIG. 3A).

Results of the above-mentioned (B) showed that virions obtained from SOCS1-introduced cells were similarly infectious as control viruses in Jurkat cells when the same amounts of virus were infected (reference: FIG. 3B). From these results, it was found that SOCS1 enhanced mature and infectious HIV-1 particle formation.

From the results of the above-mentioned (C), it was confirmed that overexpressed SOCS1 had no influence on the transcription of these reporter construct.

From the results above, it was confirmed that SOCS1 increased the replication of HIV-1 via posttranscriptional mechanisms during the production of virus.

EXAMPLE 4

(Elucidation of the Direct Interaction Between HIV-1 and SOCS1)

From the results of the above-mentioned Examples 1-3, it was confirmed that SOCS1 increased the production of HIV-1 via a mechanism after transcription of SOCS1. Furthermore, whether SOCS1 directly binds with HIV-1 Gag or not was confirmed in this Example. The details are as follows:

(A) Extracts of 293T cells transfected with either empty vector or Gag-FLAG were subjected to pull-down analyses using glutathione-agarose beads with GST-SOCS1 in the presence of 10 ng/ml RNase followed by immunoblotting with anti-FLAG antibodies.

(B) Extracts of 2937 cells transiently expressing myc-SOCS1 and Gag-FLAG were subjected to immunoprecipitation with anti-FLAG monoclonal antibodies in the presence of 10 ng/ml RNase followed by immunoblotting analysis with either anti-FLAG or anti-myc polyclonal antibodies.

(C) 293T cells were transiently transfected with Gag-FLAG, and cell lysates were then subjected to immunoprecipitation with anti-FLAG antibodies followed by immunoblotting with an antibody directed against endogenous SOCS1.

(E) 293T cells expressing various myc-tagged SOCS1 mutants (schematically depicted in FIG. 4D) were analyzed by GST pull-down analysis with either GST or GST-Gag recombinant protein.

(F) GST fusion proteins (GST-MA, GST-CA, GST-NC, GST-p6, GST-Δp6 and GST-Gag) were bound to glutathione beads and incubated with cell lysates from 293T cells expressing myc-SOCS1 in the presence of 10 ng/ml RNase followed by immunoblottinq with anti-myc antibodies.

(G) 293T cells were transfected with myc-SOCS1 and cotransfected with Gag-FLAG, GagΔMA-FLAG, GagΔNC-FLAG, or GagΔMAΔNC-FLAG. At 24 hours after transfection, cell lysates treated with 10 μg/ml RNase were subjected to communoprecipitation with anti-myc monoclonal antibodies followed by immunoblotting with anti-FLAG or anti-myc polyclonal antibodies.

(H) 293T cells were transfected with wild-type Gag, ΔMA-src, or ΔNC-LZ ($Z_{IL}$-P6) and cotransfected with either control vector or SOCS1. Supernatant virus particles were then collected after 24 hours and subjected to immunoblotting with anti-p24 antibody.

(I) HeLa cells were transiently transfected with Gag-GFP. After 24 hours, the cells were fixed, permeabilized, and immunostained with anti-SOCS1 polyclonal antibody followed by fluorescently labeled secondary antibodies before confocal microscopy.

From the results of the above-mentioned (A), p55 Gag specifically coprecipitated with GST-SOCS1 (reference: FIG. 4A)

The results of the above-mentioned (B) and (C) showed coimmunoprecipitation of both ectopically expressed-myc-tagged SOCS1 and endogenous SOCS1 with FLAG-labeled Gag in 293T cells (reference: FIG. 4B and C).

From the results of the above-mentioned (E), a SOCS mutant (ΔN-SH2) whose both N-terminal and SH2 domain were deleted, could not bind with p55 Gag. On the other hand, the deletion of N-terminal or SOCS-box did not influence on the binding of SOCS1 and Gag in 293T cells (reference: FIG. 4E). In addition, a variant R105E of SOCS1 (a variant with collapsed SH2 function to interact with phosphorylated tyrosine) could bind with Gag (reference: FIG. 4E). Thus, the SH2 domain was found important for the interaction between SOCS1 and HIV-1 Gag irrespective of the status of Gag phosphorylation.

From the results of the above-mentioned (F) and (G), it was found that SOCS1 interacted with Gag via MA and NC domain (reference: FIGS. 4F and G).

From the results of above-mentioned (H), it was found that the overexpression of SOCS1 could increase the particle formation of both wild type Gag and ΔNC-LZ, but could not increase the particle formation of ΔMa-src (reference: FIG. 4H). Thus, it became clear that the functional interaction between SOCS1 and HIV-1 Gag is mediated through MA.

From the results of the above-mentioned (I), it was found that endogenous SOCS1 formed sporadic filament-like configuration in cytoplasm, and Gag was sporadically localized with SOCS1 in the perinuclear to the peripheral region of cells (reference: FIG. 4I).

Above results showed that SOCS1 directly interacted with HIV-1 Gag in the cytoplasm during the HIV-1 particle production.

EXAMPLE 5

(Elucidation of the Direct Interaction of SOCS1 to Gag)

From the results of above Example 4, it was confirmed that SOCS1 bound directly with HIV-1 Gag. Furthermore, from the present example, it was confirmed whether SOCS1 had roles to play in regulating the stability of Gag and the transfer of Gag to plasma membrane or not. The details are as follows:

(A) HeLa cells cotransfected with pNL4-3, and either a control vector (empty vector EV) or SOCS1 were stained with an antibody targeting anti-p24 (CA). The observation was conducted using a confocal microscopy under different interference contrast.

(B) 293T cells were transfected with either a control empty vector (EV) or myc-SOCS1 and cotransfected with pNL4-3. After 48 hours, cells were pulse-labeled with [$^{35}$S]methionine or [$^{35}$S]cysteine for 15 min and chased for the durations indicated.

From the results of the above-mentioned (A), it was confirmed that the overexpression of SOCS1 increased the Gag level in the plasma membrane when cotransfected with pNL4-3. Furthermore, the cytoplasmic Gag level in SOCS1-expressing cells was very low in comparison with that in control cells (reference: FIG. 5A). Thus, it was found that SOCS1 enhanced the transfer of Gag from cytoplasm to the plasmas membrane.

The results of the above-mentioned (B) showed that SOCS1 remarkably increased the stability of intracellular p55 Gag polyprotein as well as p24 level in the supernatant. Importantly, p24 was detectable at an earlier time point and reached maximum levels in a shorter period in the cell supernatant of SOCS1-transfected cells compared with control vector-transfected cells (reference: FIG. 5B).

As shown above, it was found that SOCS1 facilitated the intracellular transfer of newly-synthesized Gag to the cytoplasmic membrane.

EXAMPLE 6

(Inhibitory Effects on the Transfer of Gag to the Cytoplasmic Membrane and the HIV-1 Particle Production with an Inhibitory Substance of SOCS1)

The inventors of the present invention have considered that a substance which is able to inhibit the interaction between SOCS1 and Gag can inhibit the production of HIV-1 particles from detailed examinations of the above-mentioned Examples 1-5. Then, the inventors of the present invention have examined the effects of siRNAs which can specifically inhibit the translation of SOCS1 gene. The details are as follows:

(A) 293T cells were transfected with either control siRNA (sequence No. 1: UCGUAUGUUGUGUGGAAUU) or two different SOCS1-specific siRNAs I (sequence No. 2: UCGAGCUGCUGGAGCACUA) or II (sequence No. 3: GGCCAGAACCUUCCUCUU) together with pNL4-3. At 48 hours after transfection, cell lysates were subjected to immunoblotting analysis with the indicated antibodies.

(B) The cell supernatants of the above-mentioned (A) were subjected to ELISA analysis of p24 levels.

(C) 293T cells were transfected with pNL4-3 and cotransfected with control-siRNA, SOCS1-siRNAI alone, or SOCS1-siRNAI plus siRNA-resistant myc-SOCS1. After 48 hours, cell supernatants were collected and subjected to p24 ELISA.

(D) HeLa cells were transfected with control siRNA or SOCS1-specific siRNA I and cotransfected with GFP-Gag. At 48 hours after transfection, the cells were subjected to confocal microscopy.

(E) HeLa cells were transfected with Sag-CFP and SOCS1-siRNA constructs (SOCS1 specific siRNA I) for 48 hours. Cells were then fixed and subjected to immunofluorescent analysis with indicated antibodies followed by DAPI staining (Scale bars: 10 mm).

(F) HeLa cells were transfected with Cag-GFP and cotransfected with either control-siRNA or SOCS1-siRNA I. After 36 hours, the cells were treated with a mock solution, 10 mM $NH_4Cl$ or 10 μM MG132 for another 16 hours. Cell were then harvested and subjected to immunoblotting analysis with anti-GCF or anti-β-actin antibodies.

(G) Jurkat cells were infected with a retroviral vector encoding control siRNA, SOCS1-specific siRNA I or siRNA II. After selection with puromycin, the cells were then infected with HIV-$1_{NL4-3}$ (multiplicity of infection, 0.1), and p24 antigen levels in cell supernatant were measured by ELISA.

(H) Human primary CD4 T cells were separated from healthy donors and infected with lentivirus vectors encoding a control siRNA or SOCS1-specific siRNA I. The cells were then infected with HIV-$1_{NL4-3}$ (multiplicity of infection, 0.1), and p24 antigen levels in cell supernatant were measured by ELISA at the indicated time points.

The results of the above-mentioned (A) and (B) showed that SOCS1-specific siRNA construct significantly decreased SOCS1 expression in comparison with control siRNA (reference: FIG. 6A and B). It became clear that the inhibition of the HIV-1 particle production by SOCS1-specific siRNA is dependent on the level of the endogenous SOCS1.

From the results of the above-mentioned (C), the inhibitory effect of SOCS1-specific siRNA on the HIV-1particle production decreased through re-expression of siRNA-resistant SOCS1 construct (reference: FIG. 6C).

The results of the above-mentioned (D) showed that the expression of SOCS1-siRNA dramatically inhibits Gag trafficking such that Gag proteins accumulate in the perinuclear regions as large solid aggregates (FIG. 6D). This finding indicates that SOCS1 plays an essential role in the Gag trafficking from perinuclear clusters to PM.

The results of the above-mentioned (E) showed that these discrete perinuclear clusters of Gag were colocalized with lysosome markers, lysozyme and a partly with AP-3, but were not colocalized with the late stage endosome MVB marker CD63 and trans-Golgi marker TGN46 (reference: FIG. 6E).

In other words, it was found that Gag was targeted for decomposition by lysosomes when the function of SOCS1 was inhibited.

The results of above-mentioned (F) showed that the level of intracellular Gag in SOCS1-siRNA cells significantly increased by the treatment of a lysosome inhibitor $NH_4Cl$, but not by a proteasome inhibitor MG132 (reference: FIG. 6F). In addition, the results of above-mentioned (E) and (F) showed that the perinuclear clusters of Gag underwent lysosomal degradation rather than proteasomal degradation when optimal Gag transport to PM (plasma membrane) is suppressed by the inhibition of SOCS1.

The results of above-mentioned (G) and (H) showed that SOCS1 in HIV-$1_{NL4-3}$-infected Jurkat cells and human primary CD4 T cells significantly decreased, resulting in pronounced decreases in HIV-1 particle production in comparison with those in the controls (reference: FIGS. 6G, 6H).

As shown above, SOCS1 inhibitor inhibits the transfer of Gag to the cytoplasmic membrane, resulting in degrading Gag in lysosomes. Therefore, an inhibitor inhibiting the interaction between SOCS1 and Gag is useful for inhibition of the HIV-1 particle production in human cells. Furthermore, the inhibitor can be used for the AIDS therapeutic agent and/or the AIDS onset inhibitor.

EXAMPLE 7

(Diagnostic Method of AIDS)

The inventors of the present invention have considered that the factors that patients without the onset of the disease for a long term (Long-term non-progressors: LTNP) do not develop diseases for a long term are connected with the expression level of SOCS1 in cells. Therefore, the expression level of SOCS1 was determined in long-term non-progressors, asymptomatic carrier patients (Asymptomatic carrier: AC) and AIDS patients. The details are as follows:

The expression levels of SOCS1 in the peripheral mononuclear cells obtained from long-term non-progressors, asymptomatic carrier patients and AIDS patients were determined by immunoblotting (reference: FIG. 7A).

Furthermore, the expression levels of SOCS1 in the peripheral mononuclear cells obtained from long-term non-progressors, asymptomatic carrier patients and AIDS patients were determined by RT-PCR using primers (sequence No. 7: agtatctttgcacaaaccagg: forward, sequence No. 8: cataataaagtttattacctaaactg: reverse) (reference: FIG. 7B).

The results are shown in FIG. 7A and 7B. SOCS1 levels in LTNP patients were significantly lower in comparison with the AC and the AIDS patients.

In other words, by determining expressed levels of SOCS1 in the peripheral mononuclear cells of HIV-infected patients the time of onset can be predicted and the degree of progression of AIDS can be evaluated.

BRIEF DESCRIPTION OF THE DRAWINGS

FIG. 1 shows results of Example 1.

FIG. 2A shows results of the determined quantity of p24 antigen in a cell supernatant after transfection and immunoblotting analysis of the supernatant and pellet virus.

FIG. 2B shows results of the determined quantity of p24 antigen in a cell supernatant after transfection and immunoblotting analysis of the supernatant and pellet virus.

FIG. 3A shows observed results of TEM for 293T cells introduced with pNL4-3+control vector or pNL4-3+myc-tagged SOCS1.

FIG. 3B shows results of the determined quantity of p24 antigen in a supernatant obtained from Jurkat cells after induction of virions.

FIG. 4A shows results of pull-down assay and immunoblotting for 293T cell extract introduced with the empty vector or FLAG-labeled Gag.

FIG. 4B shows results of immunoprecipitation and immunoblotting for 293T cell extract which temporarily express myc-SOCS1 and FLAG-labeled Gag.

FIG. 4C shows results of immunoprecipitation and immunoblotting for cell lysate introduced with FLAG-labeled Gag.

FIG. 4D shows results of pattern diagrams of SOCS1 variant.

FIG. 4E shows results of GST pull-down assay for 293T cells expressing various myc-taged SOCS1 variants.

FIG. 4F shows results of immunoblotting for cultured cell lysate obtained from GST-fused Gag protein and myc-SOCS1 expressing 293T cells.

FIG. 4G shows results of coimmunoprecipitation and immunoblotting for cell lysate after transfection.

FIG. 4H shows results of immunoblotting for recovered viral supernatant particles.

FIG. 4I shows observed results of stained cells with a confocal microscopy.

FIG. 5A shows observed results for cotransfected HeLa cells with a confocal microscopy (scale bar: 10 μm)

FIG. 5B shows results of pulse labeled and pursued cotransfected cells.

FIG. 6A shows results of immunoblotting for cell lysate introduced with siRNA, SOCS1-specific siRNA I or siRNA II.

FIG. 6B shows results of ELISA for cell supernatant of the above-mentioned (A).

FIG. 6C shows results of ELISA for cell supernatant cotransfected with single control siRNA, single SOCS1-specific siRNA I or SOCS1 specific-siRNA I+siRNA-resistant myc-SOCS1.

FIG. 6D shows observed results of cells after cotransfection with a confocal microscopy.

FIG. 6E shows results of immunofluorescence analysis for Gag-GFP and SOCS1-siRNA construct introduced cells and results of DAPI staining (scale bar: 10 mm).

FIG. 6F shows results of immunoblotting analysis for cells after cotransfection.

FIG. 6G shows results of determination of the quantity of p24 antigen in cell supernatant by ELISA.

FIG. 6H shows results of determination of the quantity of p24 antigen in cell supernatant obtained from HIV-$1_{NL4-3}$-infected cells by ELISA.

FIG. 7A shows results of the determined expression level of SOCS1 by immunoblotting.

FIG. 7B shows results of the determined expression level of SOCS1 by RT-PCR.

SEQUENCE LISTING

Figure 1A:
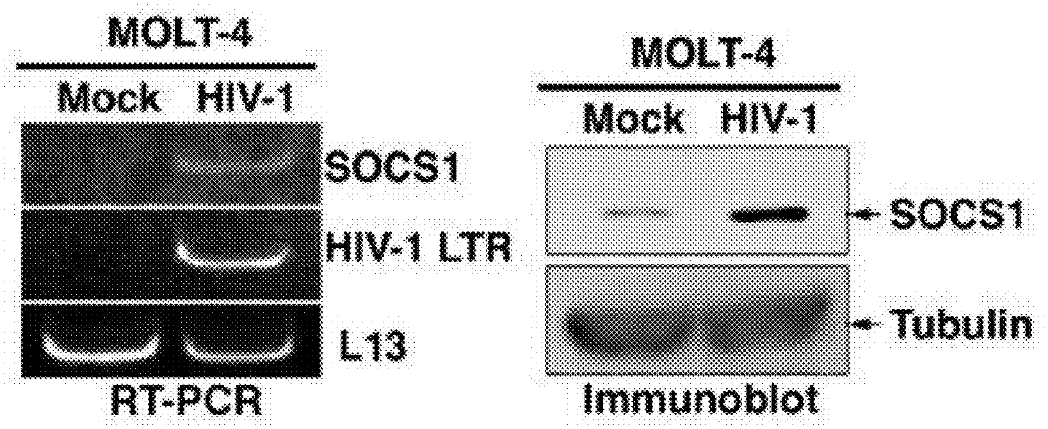
FIG. 1A shows results of semiquantitative RT-PCR and immunoblotting for total RNA and protein extract in mock- or HIV-$1_{NL4-3}$-infected MOLT-4 cells.
Figure 1B:
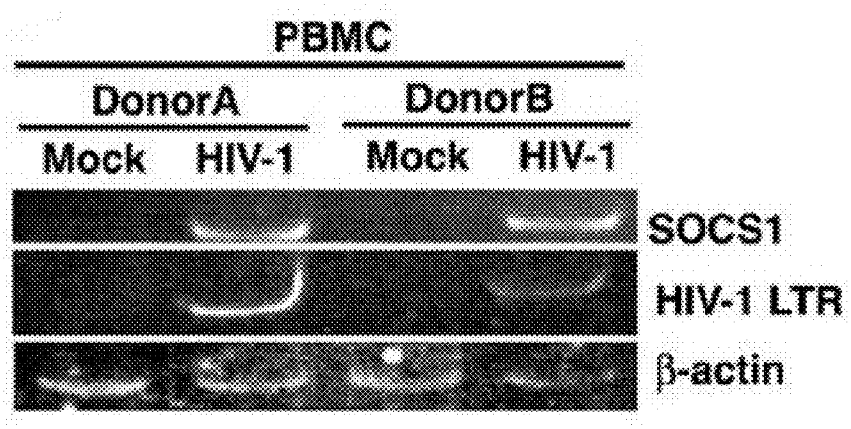
FIG. 1B shows results of semiquantitative RT-PCR of SOCS1 expression level in PBMC (the peripheral-blood mononuclear cells) derived from healthy individuals infected with mock- or HIV-$1_{NL4-3}$.
Figure 2:
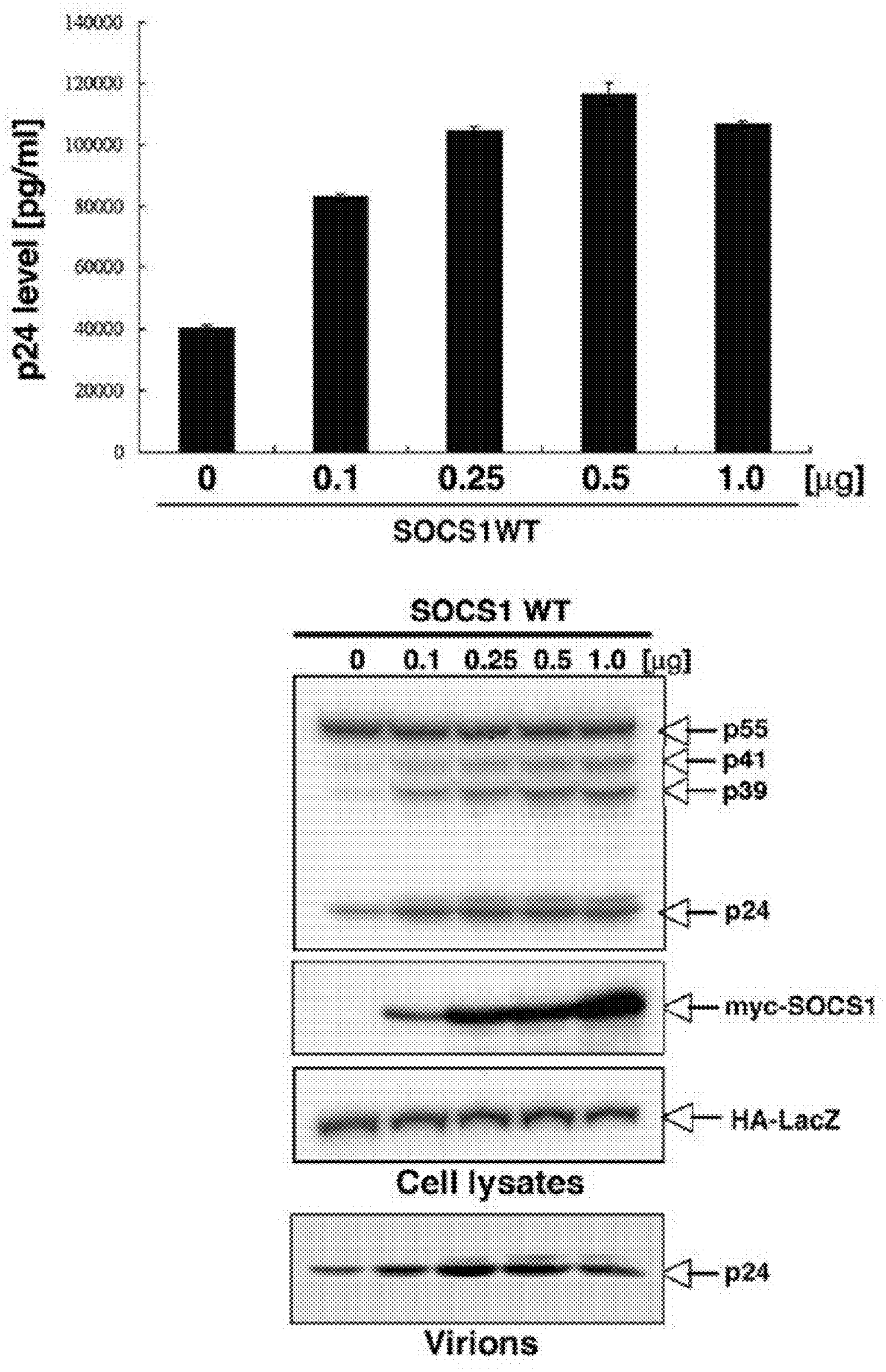
FIG. 2 shows results of Example 2.
Figure 2:
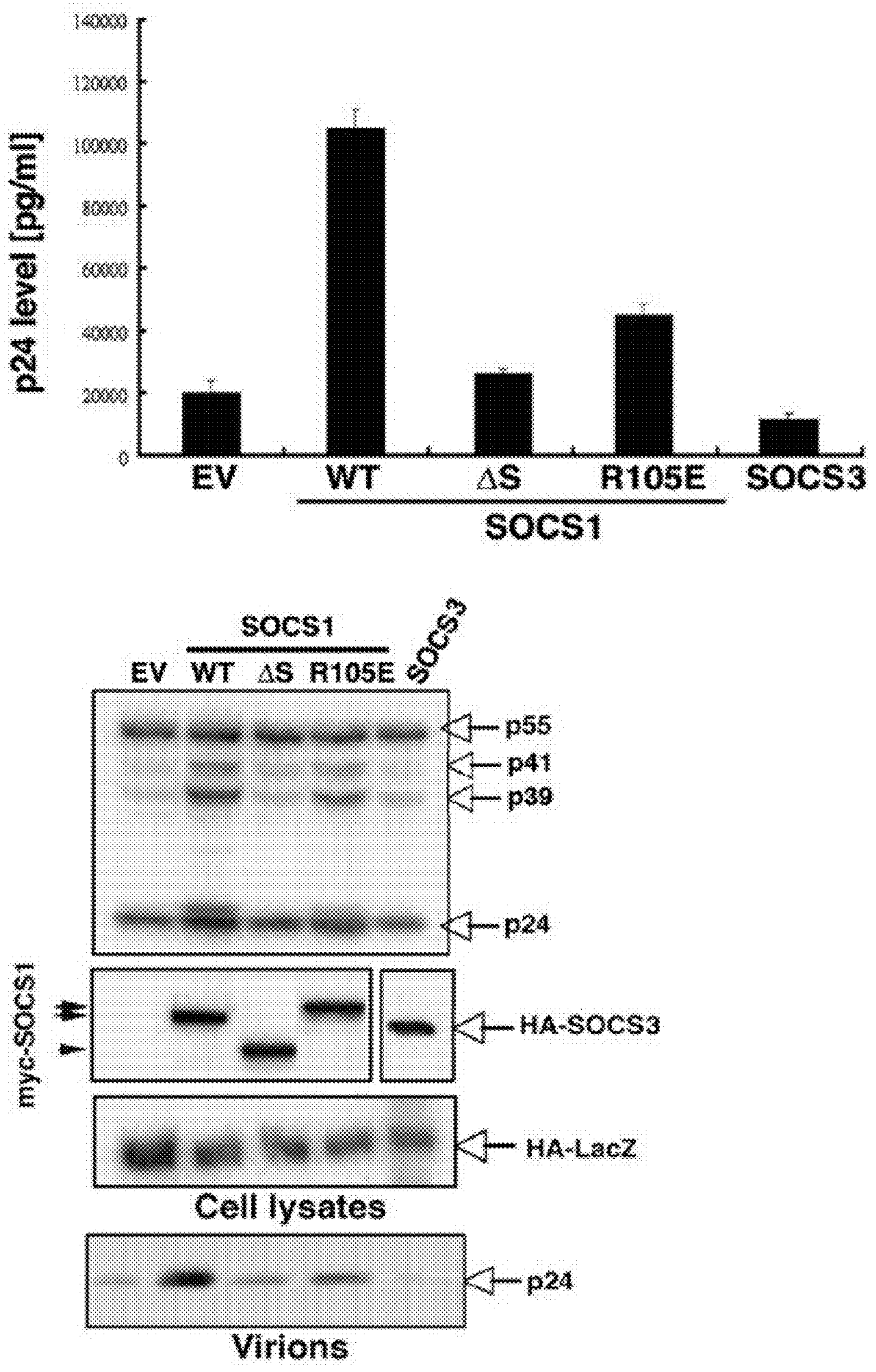
Figure 3:
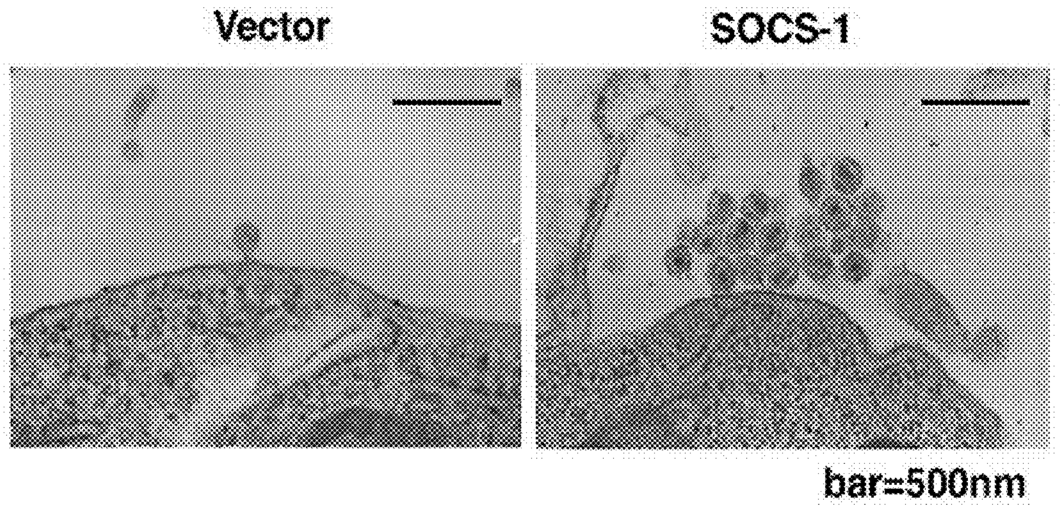
FIG. 3 shows results of Example 3.
Figure 3:
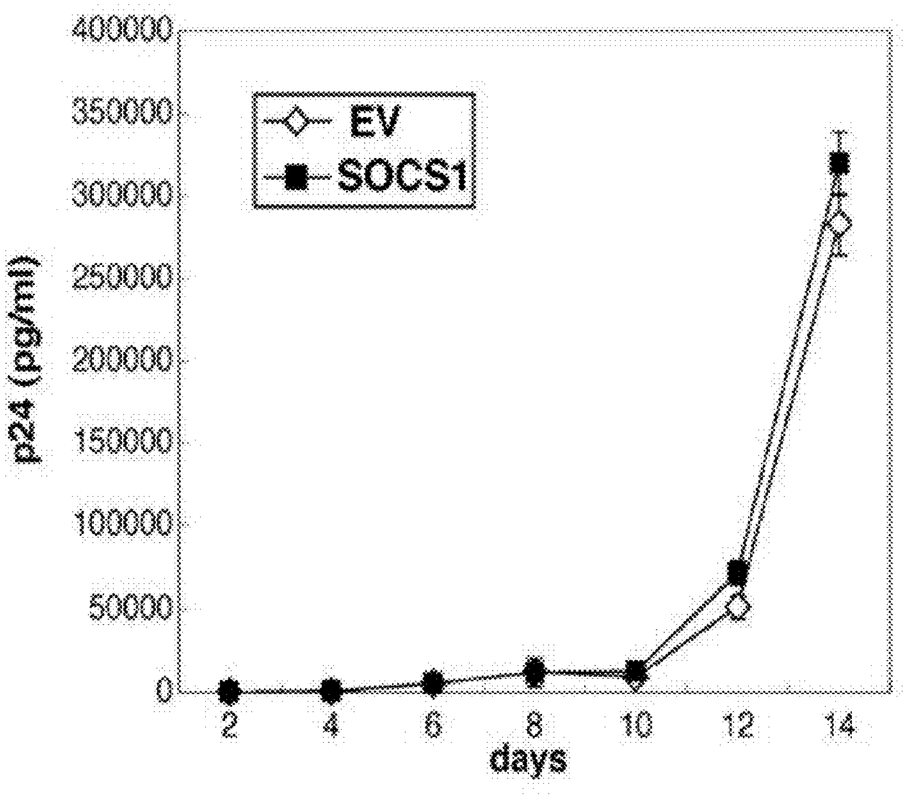
Figure 4:
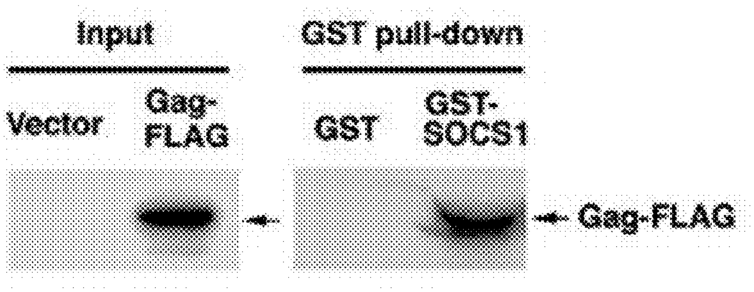
FIG. 4 shows results of Example 4.
Figure 4:
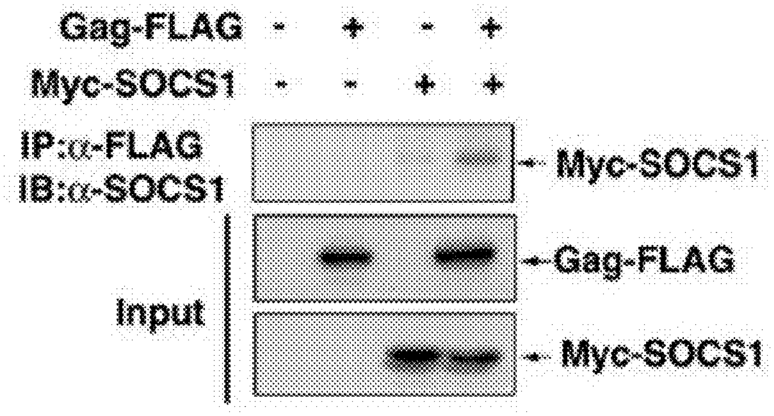
Figure 4:
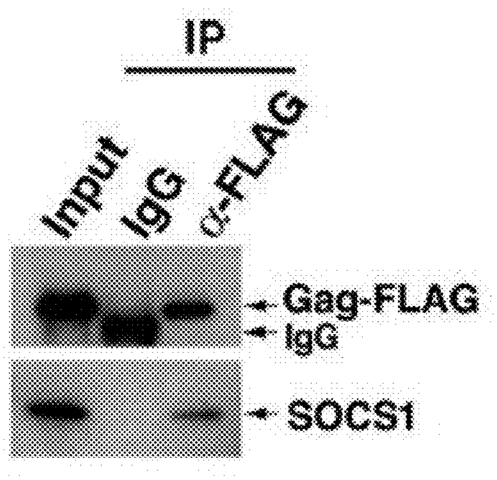
Figure 4:
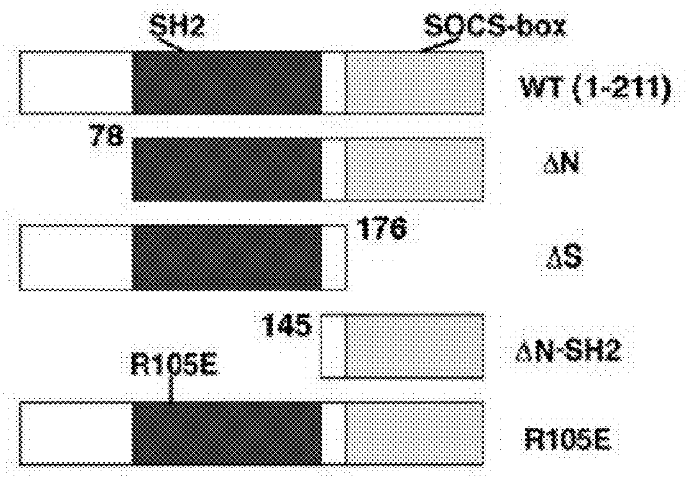
Figure 4:
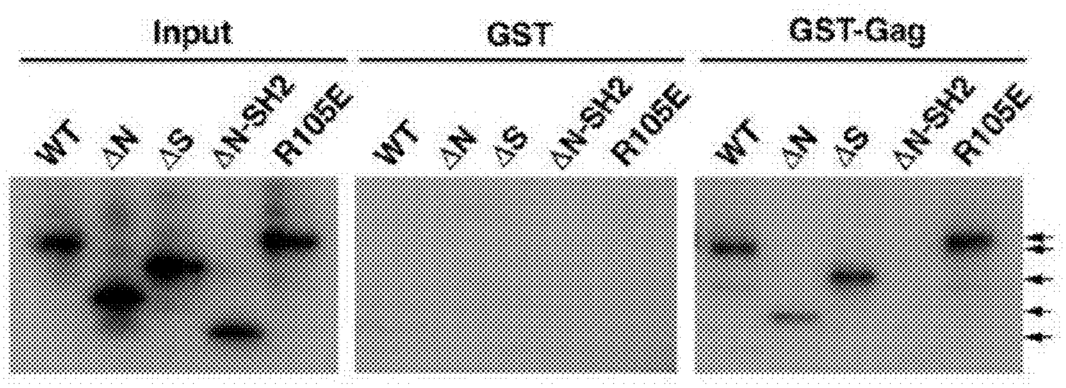
Figure 4:
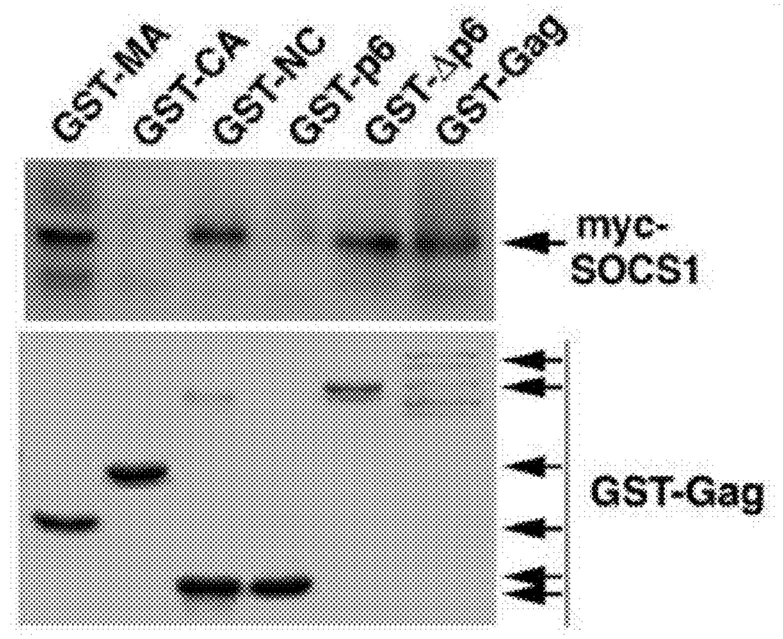
Figure 4:
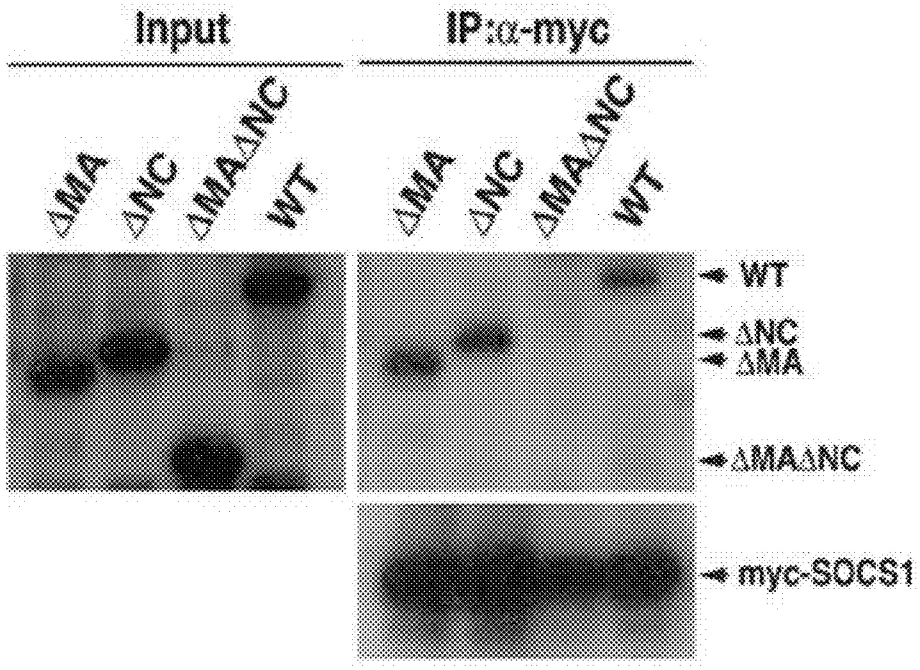
Figure 4:
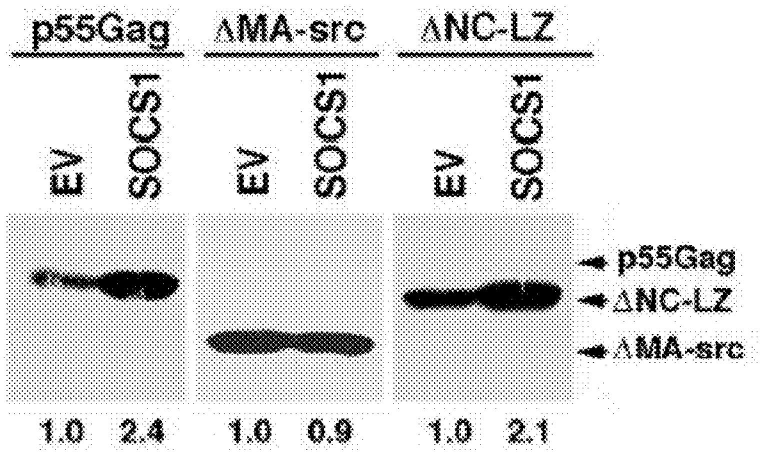
Figure 4:
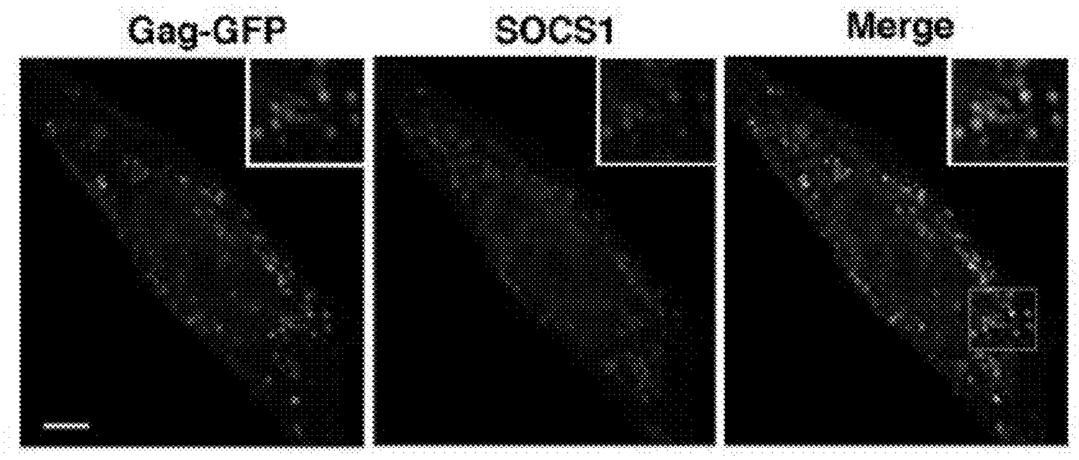
Figure 5:
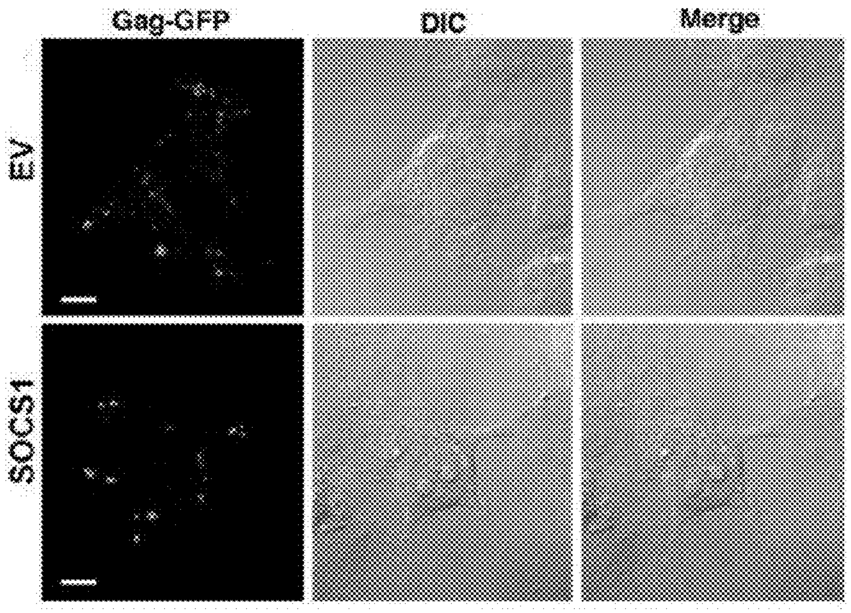
FIG. 5 shows results of Example 5.
Figure 5:
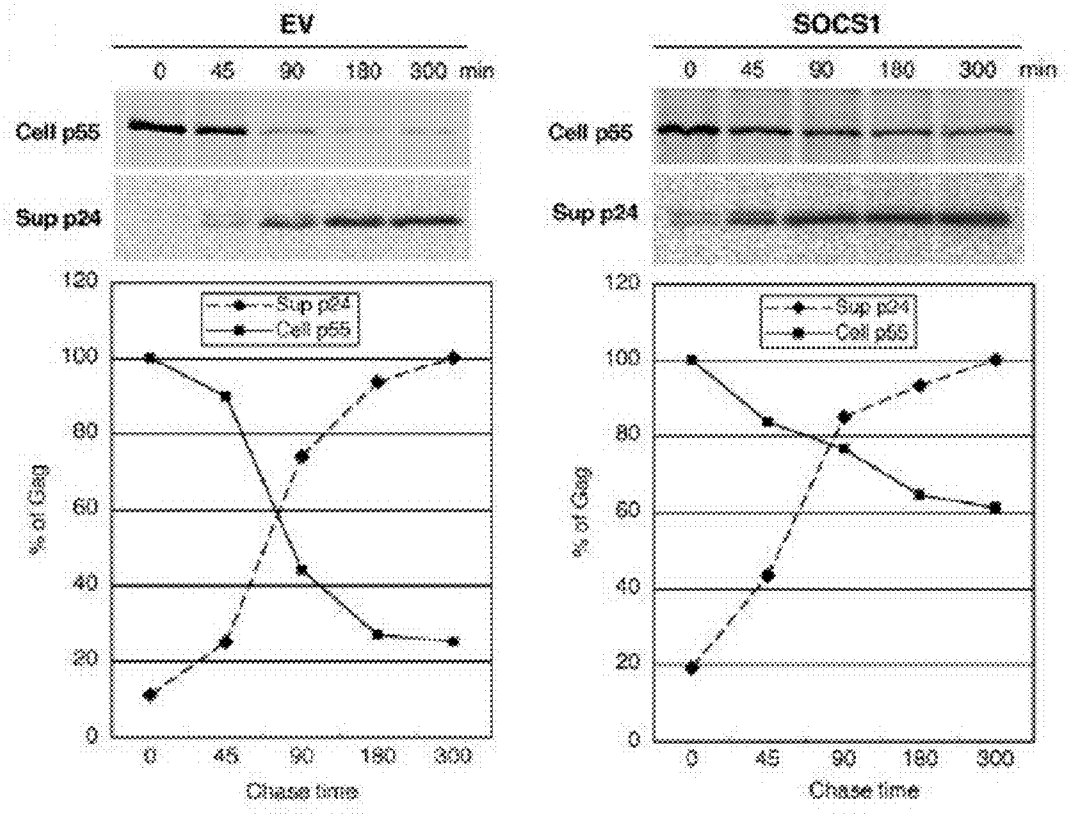
Figure 6:
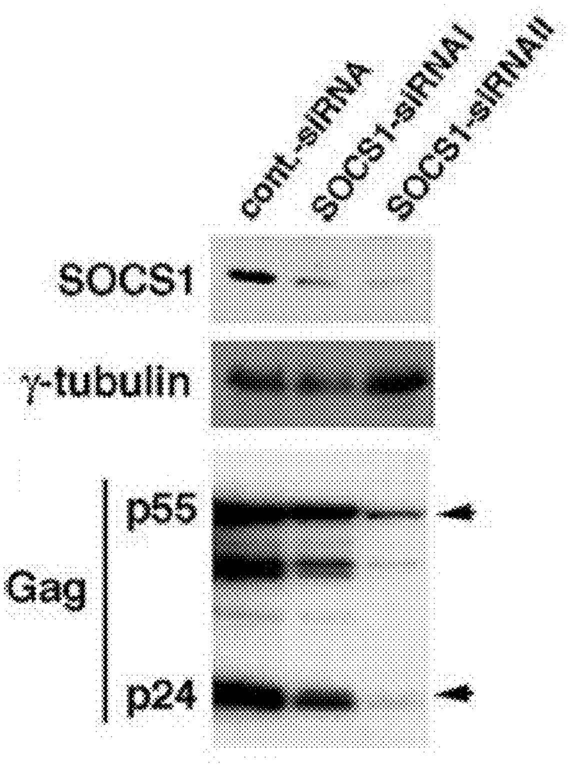
FIG. 6 shows results of Example 6.
Figure 6:
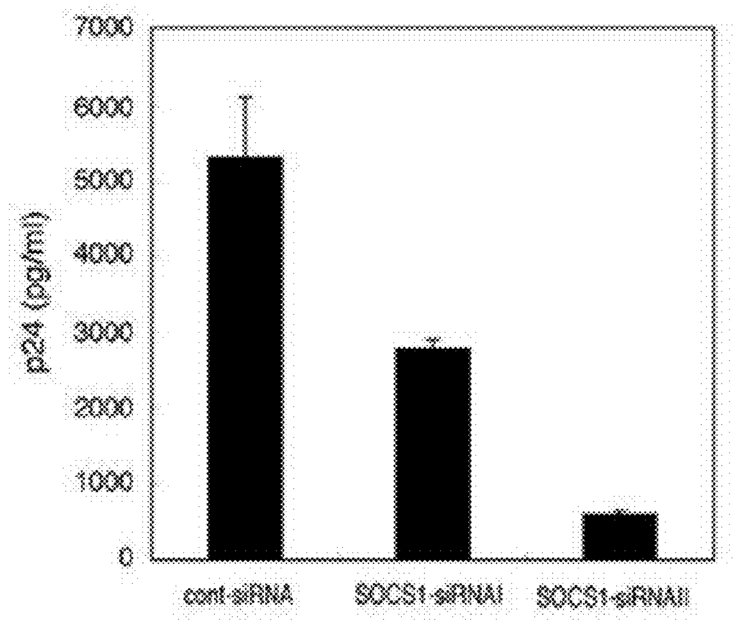
Figure 6:
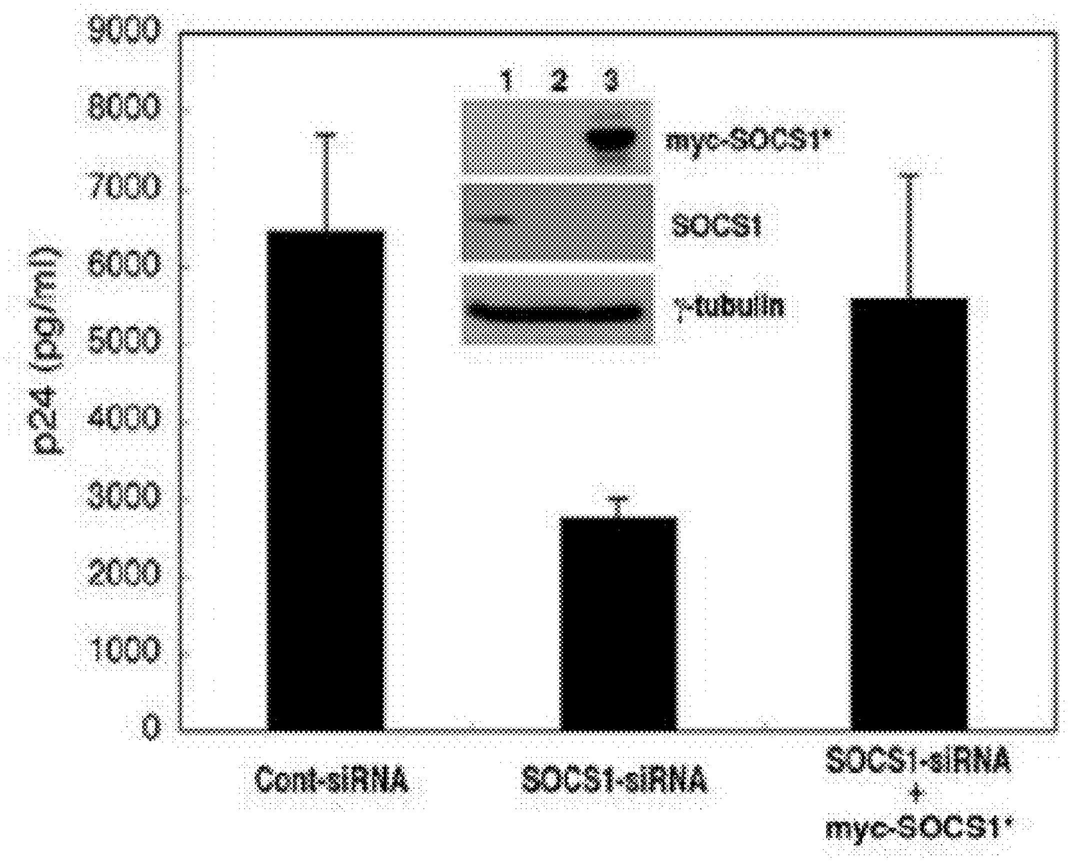
Figure 6:
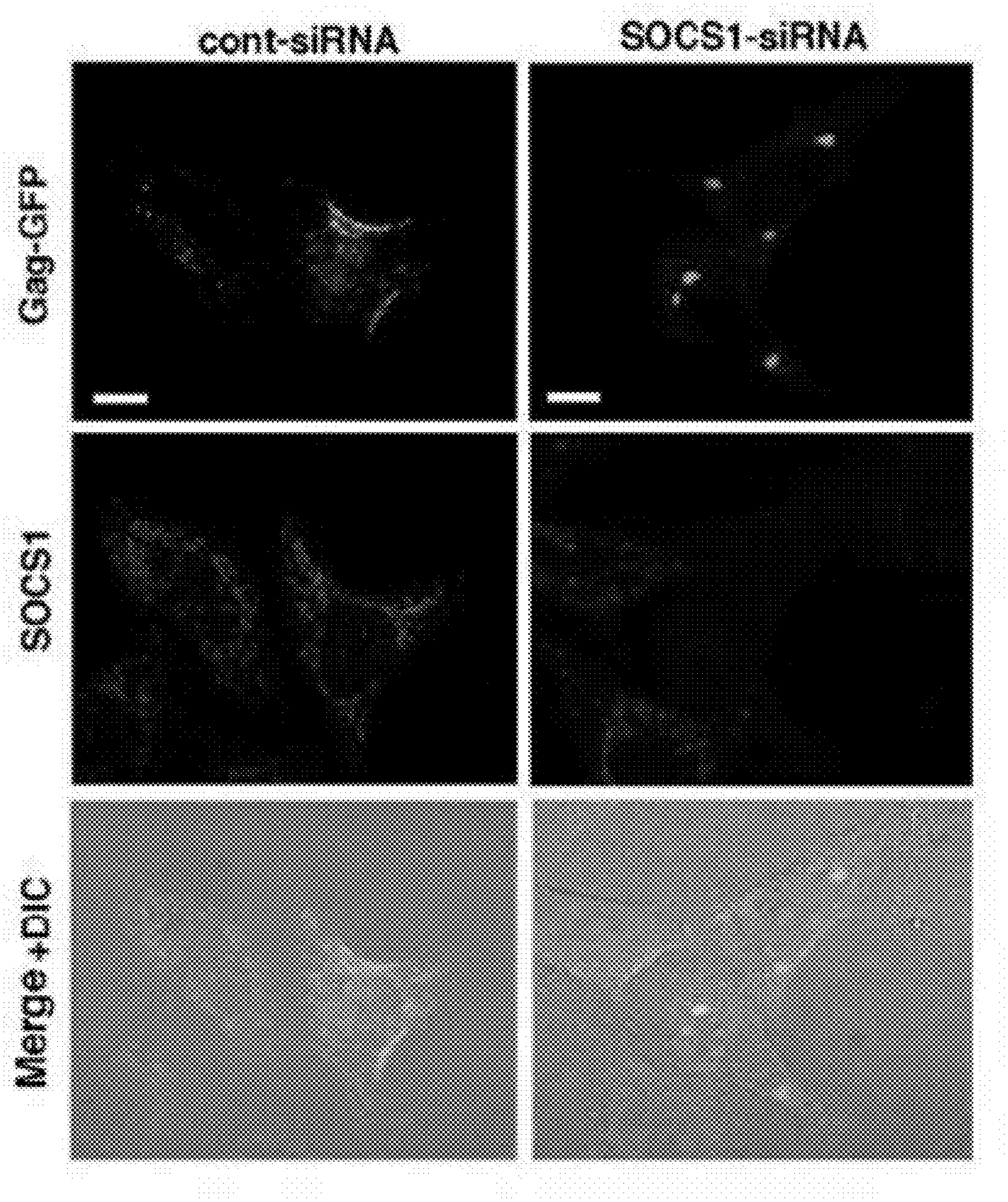
Figure 6:
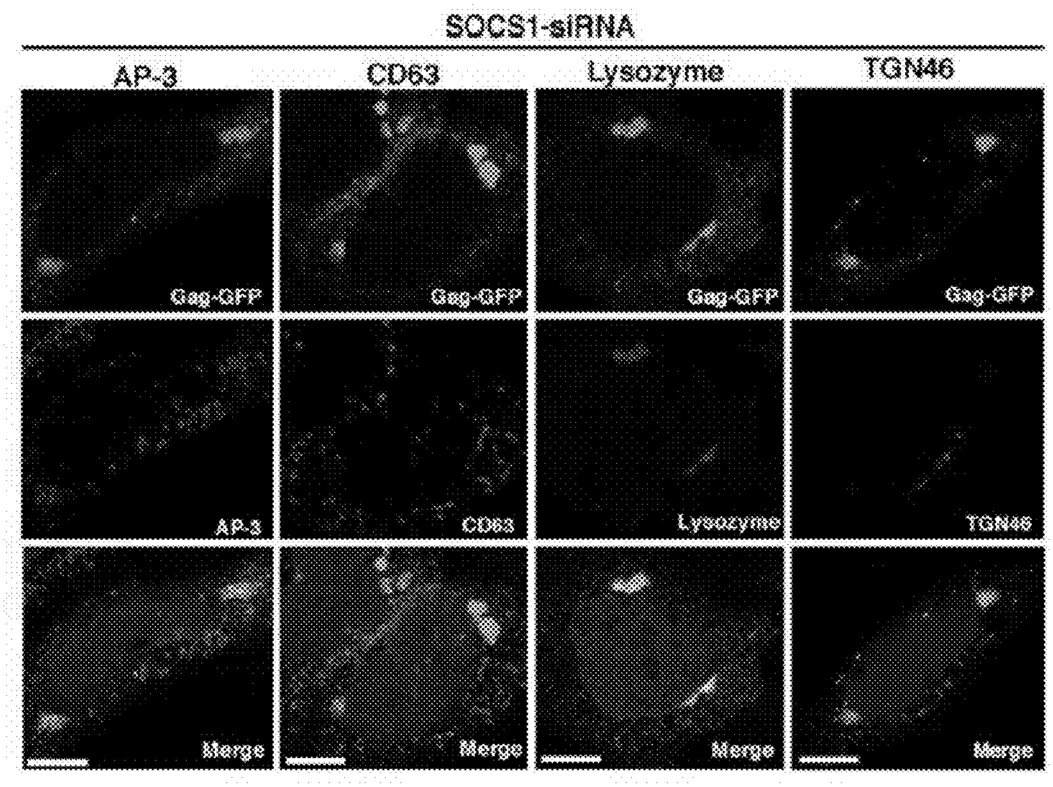
Figure 6:
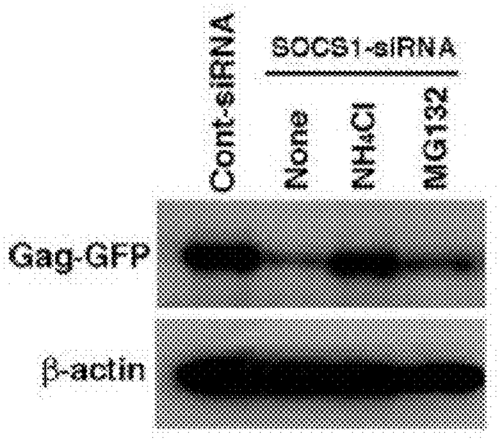
Figure 6:
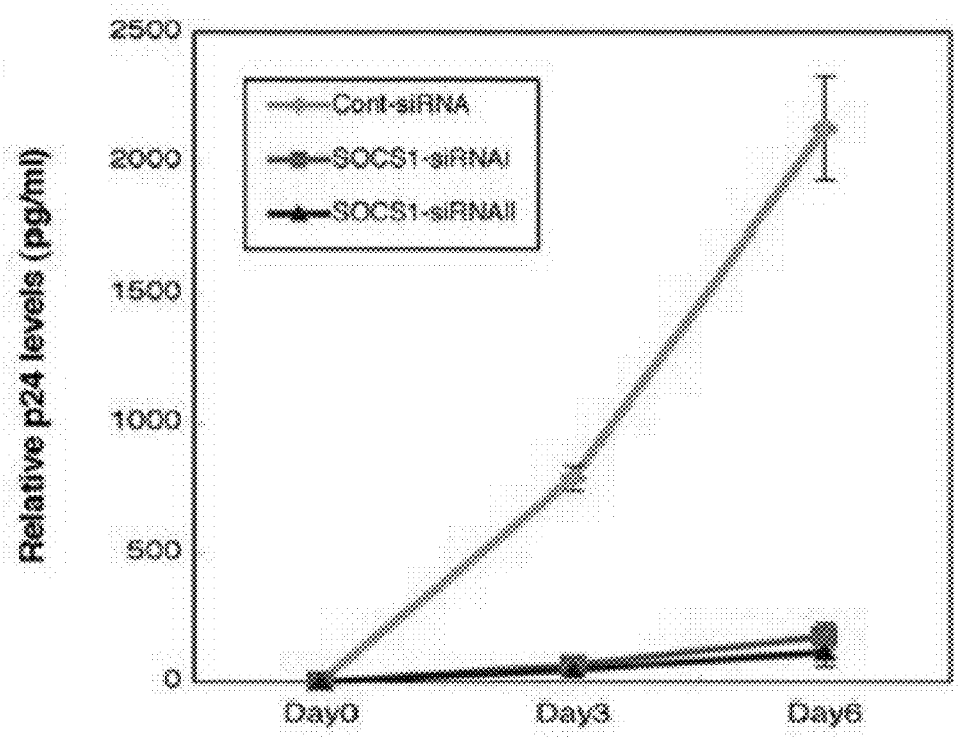
Figure 6:
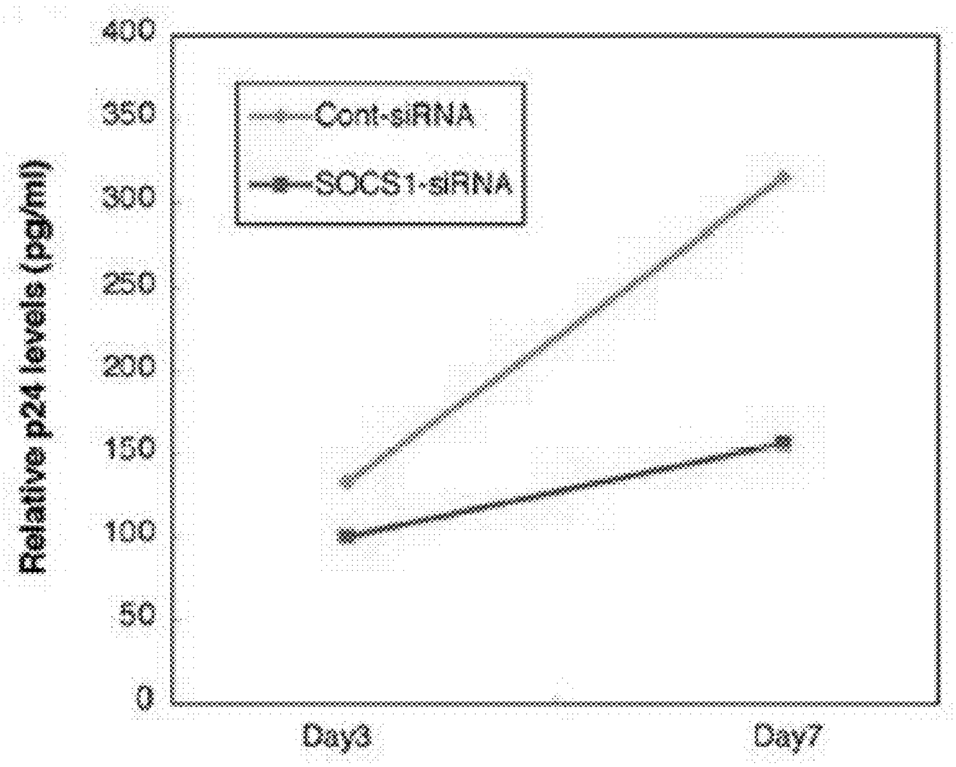
Figure 7:
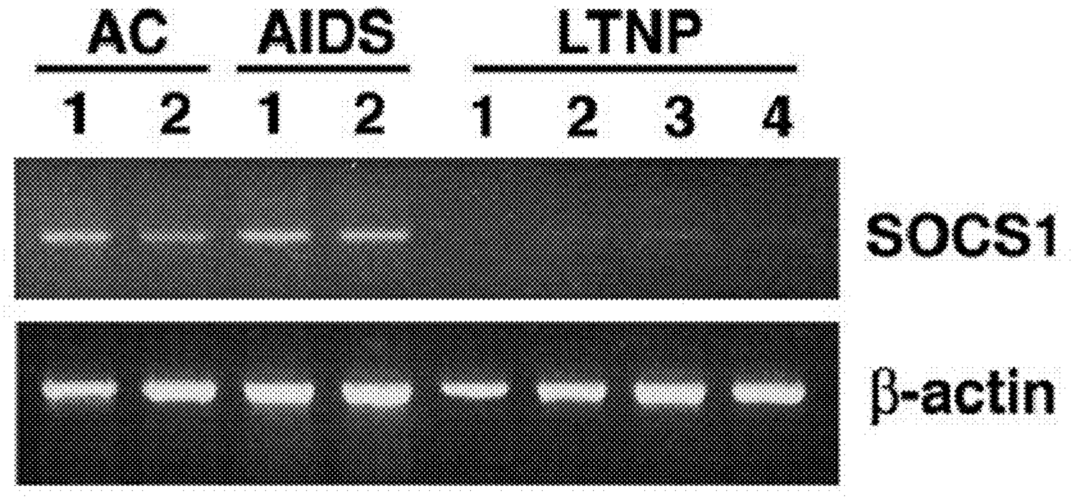
FIG. 7 shows results of Example 7.
Figure 7:
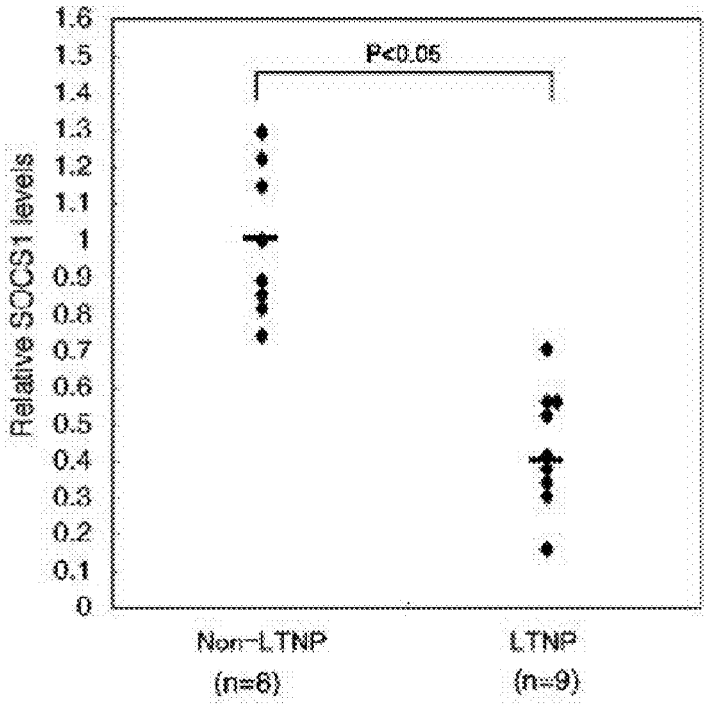

```
<160> NUMBER OF SEQ ID NOS: 8

<210> SEQ ID NO 1
<211> LENGTH: 19
<212> TYPE: RNA
<213> ORGANISM: Artificial
<220> FEATURE:
<223> OTHER INFORMATION: control siRNA suppressing interaction between
      SOCS1 and Gag

<400> SEQUENCE: 1

ucguauguug uguggaauu                                              19


<210> SEQ ID NO 2
<211> LENGTH: 19
<212> TYPE: RNA
<213> ORGANISM: Artificial
<220> FEATURE:
<223> OTHER INFORMATION: siRNA suppressing interaction between SOCS1 and
      Gag

<400> SEQUENCE: 2

ucgagcugcu ggagcacua                                              19


<210> SEQ ID NO 3
<211> LENGTH: 18
<212> TYPE: RNA
<213> ORGANISM: Artificial
<220> FEATURE:
<223> OTHER INFORMATION: siRNA suppressing interaction between SOCS1 and
      Gag

<400> SEQUENCE: 3

ggccagaacc uuccucuu                                               18


<210> SEQ ID NO 4
<211> LENGTH: 19
<212> TYPE: RNA
<213> ORGANISM: Artificial
<220> FEATURE:
<223> OTHER INFORMATION: siRNA suppressing interaction between SOCS1 and
      Gag

<400> SEQUENCE: 4

aaccaggugg cagccgaca                                              19


<210> SEQ ID NO 5
<211> LENGTH: 20
<212> TYPE: RNA
<213> ORGANISM: Artificial
<220> FEATURE:
<223> OTHER INFORMATION: siRNA suppressing interaction between SOCS1 and
      Gag

<400> SEQUENCE: 5

acgagcaucc gcgugcacuu                                             20


<210> SEQ ID NO 6
<211> LENGTH: 19
<212> TYPE: RNA
<213> ORGANISM: Artificial
<220> FEATURE:
<223> OTHER INFORMATION: siRNA suppressing interaction between SOCS1 and
      Gag

<400> SEQUENCE: 6
```

-continued cuaccugagc uccuucccc 19

<210> SEQ ID NO 7
<211> LENGTH: 21
<212> TYPE: DNA
<213> ORGANISM: Artificial
<220> FEATURE:
<223> OTHER INFORMATION: Primer for detecting expression levels of SOCS1

<400> SEQUENCE: 7
agtatctttg cacaaaccag g 21

<210> SEQ ID NO 8
<211> LENGTH: 26
<212> TYPE: DNA
<213> ORGANISM: Artificial
<220> FEATURE:
<223> OTHER INFORMATION: Primer for detecting expression levels of SOCS1

<400> SEQUENCE: 8
cataataaag tttattacct aaactg 26

What is claimed is:

1. A method for screening an inhibitor against the binding between SOCS1 and Gag comprising processes of:

1) expressing Gag or a modified Gag, and SOCS1 or a modified SOCS1 in cells;
2) introducing a compound into the cells; and
3) detecting inhibition of the binding between SOCS1 and Gag; wherein the modified Gag retains MA and NC domain structure; and wherein the modified SOCS1 retains SOCS-box and SH domain structure.

2. The screening method according to claim 1, comprising the processes of introducing a gene encoding said Gag or modified Gag, and/or said SOCS1 or modified SOCS1 into said cells and expressing said Gag or modified Gag, and/or said SOCS1 or modified SOCS1 in the cells.

3. The screening method according to claim 1 comprising the method for detecting inhibition of the binding between said SOCS1 and Gag by any one of the methods of:

1) RT-PCR;
2) immunoblotting;
3) SAGE;
4) immunoprecipitation;
5) pull-down assay;
6) ELISA; and
7) Western blotting.

4. The screening method according to claim 1, wherein the compound is an AIDS therapeutic agent and/or an AIDS onset inhibitor.

5. A method for screening siRNA suppressing or inhibiting the binding between SOCS1 and Gag comprising the following processes of:

1) introducing a SOCS1 gene or a modified SOCS1 gene into cells;
2) introducing a candidate siRNA into the cells; and
3) detecting the SOCS1 or modified SOCS1 gene dosage.

6. A screening method according to claim 5 comprising further introducing the Gag gene or the modified Gag gene into said cells.

7. The screening method according to claim 1, wherein the compound inhibits SOCS1 before binding of SOCS1 with Gag.

8. The screening method according to claim 1, wherein the compound is a siRNA.

9. The screening method according to claim 8, wherein the siRNA targets a gene encoding said SOCS1 or modified SOCS1 before the binding between SOCS1 and Gag.

* * * * *